United States Patent
Guo et al.

(10) Patent No.: US 9,968,258 B2
(45) Date of Patent: May 15, 2018

(54) IMAGING FLUORESCENCE OR LUMINESCENCE LIFETIME

(75) Inventors: Jian Guo, Milpitas, CA (US); Sameer Sonkusale, Arlington, MA (US)

(73) Assignee: Tufts University, Medford, MA (US)

( * ) Notice: Subject to any disclaimer, the term of this patent is extended or adjusted under 35 U.S.C. 154(b) by 820 days.

(21) Appl. No.: 14/344,507

(22) PCT Filed: Sep. 12, 2012

(86) PCT No.: PCT/US2012/054897
§ 371 (c)(1),
(2), (4) Date: Mar. 10, 2015

(87) PCT Pub. No.: WO2013/040058
PCT Pub. Date: Mar. 21, 2013

(65) Prior Publication Data
US 2015/0173621 A1    Jun. 25, 2015

Related U.S. Application Data

(60) Provisional application No. 61/533,456, filed on Sep. 12, 2011.

(51) Int. Cl.
| | | |
|---|---|---|
| A61B 5/00 | (2006.01) |
| G01N 21/64 | (2006.01) |
| G01J 1/44 | (2006.01) |
| G01J 3/28 | (2006.01) |
| H01L 27/146 | (2006.01) |
| G01J 3/44 | (2006.01) |

(52) U.S. Cl.
CPC ............ *A61B 5/0071* (2013.01); *A61B 5/444* (2013.01); *G01J 1/44* (2013.01); *G01J 3/2803* (2013.01); *G01J 3/4406* (2013.01); *G01N 21/6408* (2013.01); *G01N 21/6456* (2013.01); *G01N 21/6486* (2013.01); *H01L 27/1461* (2013.01); *A61B 5/6801* (2013.01)

(58) Field of Classification Search
CPC ..... A61B 5/0071; A61B 5/444; A61B 5/6801; G01J 1/44; G01J 3/2803; G01J 3/4406; G01N 21/6408
USPC ................................ 600/306, 312, 321, 476
See application file for complete search history.

(56) References Cited

U.S. PATENT DOCUMENTS

| | | | | |
|---|---|---|---|---|
| 5,196,709 A | * | 3/1993 | Berndt | G01N 21/6408 250/458.1 |
| 6,673,596 B1 | * | 1/2004 | Sayler | C12Q 1/02 422/504 |
| 7,126,126 B2 | * | 10/2006 | Schyler | A61B 6/037 250/363.03 |
| 7,286,867 B2 | * | 10/2007 | Schlyer | A61B 6/037 324/318 |
| 7,797,119 B2 | * | 9/2010 | de Boer | A61B 5/0059 702/69 |
| 7,808,063 B2 | * | 10/2010 | Boettiger | C23C 4/12 257/432 |
| 7,961,315 B2 | * | 6/2011 | Cunningham | G01N 21/6428 356/317 |

(Continued)

*Primary Examiner* — Christopher A Flory
(74) *Attorney, Agent, or Firm* — Fish & Richardson P.C.

(57) ABSTRACT

Devices for use in fluorescence or luminescence lifetime imaging include a chip featuring an imaging region that includes a photodetector for receiving optical signals, and a time-to-digital converter for providing digital phase output based on the received optical signals.

21 Claims, 11 Drawing Sheets

(56) References Cited

U.S. PATENT DOCUMENTS

| | | | |
|---|---|---|---|
| 2003/0062485 A1* | 4/2003 | Fernandez | G01N 21/274 250/458.1 |
| 2004/0165778 A1* | 8/2004 | Cartlidge | G01N 21/6458 382/211 |
| 2004/0169854 A1* | 9/2004 | Vo-Dinh | G01J 3/2889 356/301 |
| 2005/0020894 A1* | 1/2005 | Norris | A61B 5/14551 600/323 |
| 2005/0113667 A1* | 5/2005 | Schlyer | A61B 6/037 600/411 |
| 2005/0136448 A1* | 6/2005 | Hartel | C12Q 1/6816 435/6.12 |
| 2005/0225649 A1* | 10/2005 | Shinotsuka | H04N 5/35518 348/226.1 |
| 2005/0264813 A1* | 12/2005 | Giakos | B82Y 20/00 356/369 |
| 2006/0014228 A1* | 1/2006 | Simpson | C12Q 1/02 435/7.32 |
| 2006/0051816 A1* | 3/2006 | Hsieh | G01N 33/56966 435/7.9 |
| 2006/0114296 A1* | 6/2006 | Gascoyne | B01L 3/50273 347/73 |
| 2006/0134644 A1* | 6/2006 | Hartel | C12Q 1/6816 435/6.12 |
| 2006/0281067 A1* | 12/2006 | Simpson | C12Q 1/02 435/4 |
| 2007/0018116 A1* | 1/2007 | Lustenberger | G01N 21/6458 250/458.1 |
| 2007/0034778 A1* | 2/2007 | Lustenberger | G01S 17/89 250/208.1 |
| 2007/0038206 A1* | 2/2007 | Altshuler | A46B 15/0036 606/20 |
| 2007/0198004 A1* | 8/2007 | Altshuler | A46B 15/0036 606/9 |
| 2007/0213696 A1* | 9/2007 | Altshuler | A46B 15/0036 606/9 |
| 2007/0213698 A1* | 9/2007 | Altshuler | A46B 15/0036 606/12 |
| 2007/0239142 A1* | 10/2007 | Altshuler | A46B 15/0036 606/9 |
| 2007/0239143 A1* | 10/2007 | Altshuler | A46B 15/0036 606/9 |
| 2008/0037008 A1* | 2/2008 | Shepard | G01N 21/6408 356/73 |
| 2008/0038771 A1* | 2/2008 | Taylor | G01N 33/96 435/40.5 |
| 2008/0050013 A1* | 2/2008 | Munro | G01S 13/89 382/154 |
| 2008/0278722 A1* | 11/2008 | Cunningham | G01N 21/6428 356/317 |
| 2009/0021617 A1* | 1/2009 | Oggier | G01S 17/89 348/294 |
| 2009/0093807 A1* | 4/2009 | Hyde | A61B 5/0071 606/34 |
| 2010/0056928 A1* | 3/2010 | Zuzak | A61B 5/0071 600/476 |
| 2010/0059696 A1* | 3/2010 | Heintzmann | G02B 21/0056 250/550 |
| 2010/0075361 A1* | 3/2010 | Mattoussi | G01N 21/6408 435/29 |
| 2010/0078569 A1* | 4/2010 | Jarron | A61B 6/037 250/363.04 |
| 2010/0106041 A1* | 4/2010 | Ghovanloo | A61B 5/0031 600/544 |
| 2010/0196914 A1* | 8/2010 | Hsieh | G01N 33/56966 435/6.1 |
| 2011/0104071 A1* | 5/2011 | Lee | A61B 5/0071 424/9.6 |
| 2011/0180726 A1* | 7/2011 | Gratton | G01J 3/4406 250/459.1 |
| 2011/0275538 A1* | 11/2011 | Sonkusale | G01N 33/4836 506/10 |
| 2011/0300490 A1* | 12/2011 | Rachet | G02B 21/0032 430/322 |
| 2011/0312075 A1* | 12/2011 | Facer | B01L 3/5027 435/287.2 |
| 2011/0312545 A1* | 12/2011 | Silverbrook | B01L 3/5027 506/16 |
| 2011/0312546 A1* | 12/2011 | Azimi | B01L 3/5027 506/16 |
| 2011/0312572 A1* | 12/2011 | Moini | B01L 3/5027 506/16 |
| 2011/0312573 A1* | 12/2011 | Silverbrook | B01L 3/5027 506/16 |
| 2011/0312574 A1* | 12/2011 | Moini | B01L 3/5027 506/16 |
| 2011/0312579 A1* | 12/2011 | Silverbrook | B01L 3/5027 506/16 |
| 2011/0312582 A1* | 12/2011 | Silverbrook | B01L 3/5027 506/16 |
| 2011/0312583 A1* | 12/2011 | Facer | B01L 3/5027 506/16 |
| 2011/0312585 A1* | 12/2011 | Silverbrook | B01L 3/5027 506/16 |
| 2011/0312615 A1* | 12/2011 | Azimi | B01L 3/5027 506/37 |
| 2011/0312616 A1* | 12/2011 | Azimi | B01L 3/5027 506/37 |
| 2011/0312622 A1* | 12/2011 | Azimi | B01L 3/5027 506/39 |
| 2011/0312841 A1* | 12/2011 | Silverbrook | B01L 3/5027 506/40 |
| 2011/0320174 A1* | 12/2011 | Ragan | G01N 21/6408 702/189 |
| 2012/0220022 A1* | 8/2012 | Ehrlich | G01N 15/14 435/286.2 |
| 2012/0224053 A1* | 9/2012 | Vykoukal | B01L 3/502715 348/135 |
| 2012/0283575 A1* | 11/2012 | Rao | A61B 5/015 600/476 |
| 2012/0313803 A1* | 12/2012 | Dosho | H03M 1/50 341/166 |
| 2014/0226166 A1* | 8/2014 | Kumar | G01T 1/1647 356/601 |
| 2016/0025632 A1* | 1/2016 | Lee | A61B 5/0071 506/10 |

* cited by examiner

IMAGING FLUORESCENCE OR LUMINESCENCE LIFETIME

CROSS-REFERENCE TO RELATED APPLICATIONS

This application is a National Stage application under 35 U.S.C. § 371 of international application number PCT/US2012/054897, filed on Sep. 12, 2012, which claims priority to US Patent Application Ser. No. 61/533,456, filed on Sep. 12, 2011, the entire contents of which is are hereby incorporated by reference.

TECHNICAL FIELD

This disclosure relates to imaging fluorescence or luminescence lifetime, in particular, using a monolithic chip that integrates an image sensor and provides direct digital phase readout.

BACKGROUND

The lifetime of excited fluorescent or luminescent dyes, or of an intrinsic autofluorescent response to an excitation light, is highly sensitive and selective to chemical and/or biological properties of the surrounding environment of the dyes or autofluorescent material in the sample. Images of the fluorescence/luminescence lifetime can be used for understanding these chemical or biological properties. Time-correlated single-photon counting (TCSPC) or frequency-domain phase measurement can be used for obtaining the images. In particular, TCSPC is a histogram-based method that uses ultra-fast laser pulse with sub-nanosecond resolution for fluorescence/luminescence excitation and obtains the fluorescent lifetime image through image reconstruction. The frequency-domain phase measurement uses a laser diode or a low-power LED as an excitation source.

SUMMARY

This disclosure features fluorescence and/or luminescence lifetime imaging systems fully integrated in a monolithic chip, e.g., a complementary metal-oxide semiconductor (CMOS) chip containing integrated circuits, that provides on-chip digital phase output (or readout), as well as methods of making and using these systems. The imaging systems can be used in time-resolved lifetime imaging applications, such as oxygen sensing for tumor detection or skin cancer scanning. In particular, the imaging systems implement frequency-domain phase-shift measurements and convert the frequency-domain phase shift into a time-domain delay via a zero-crossing detection method. The converted time-delay is quantized directly on the chip using a time-to-digital converter (TDC) configured to have a high temporal precision and a wide dynamic range. The chips are configured to allow for low-frequency signal modulation and low power consumption, and to provide a high resolution for the phase measurement.

In certain implementations, the phase readout from the chip can have a sensitivity better than 0.01 degrees at a modulation frequency of 1.2 KHz and 0.1 degrees at a modulation frequency of 1 MHz. In certain implementations, the circuits for zero crossing detection and for the TDC can have a temporal resolution of lower than 110 ps with a dynamic range greater than 400 μsec. The power consumption of the entire chips can be less than 1.2 mW. The chips provide fluorescence lifetime imaging with high temporal and spatial resolution, at a low cost, using a low power, and within a large temporal dynamic range.

In one aspect, the disclosure features devices for use in fluorescence or luminescence lifetime imaging. The devices can include integrated complementary metal-oxide semiconductor (CMOS) chips that include an imaging region and a time-to-digital converter. The imaging region includes a photodetector for receiving optical signals. The time-to-digital converter provides digital phase output based on the received optical signals.

In another aspect, the disclosure features microscopes that include a lens and an integrated complementary metal-oxide semiconductor (CMOS) chip. The CMOS chip includes an imaging region and a time-to-digital converter. The imaging region includes a photodetector for receiving optical signals that pass the lens. The time-to-digital converter provides digital phase output based on the received optical signals. In some implementations, the microscopes are oxygen sensing microscopes and the optical signals are received from a fluorescent or luminescent marker or autofluorescence in a tissue, e.g., in vivo.

In another aspect, the disclosure features scanner devices for use in detecting skin cancer. The scanners include an integrated complementary metal-oxide semiconductor (CMOS) chip that includes an imaging region and a time-to-digital converter. The imaging region includes a photodetector for receiving optical signals. The time-to-digital converter provides digital phase output based on the received optical signals. The scanners also include a display for displaying the digital phase output from the integrated CMIS chip. In some implementations, the scanners are designed to be portable, e.g., sized and configured to be hand-held.

The devices, microscopes, and scanner devices can include one or more of the following features or embodiments. The imaging region can include an array of photodetectors. The photodetectors can be photodiodes. The photodiodes can include a P+ layer buried in an N-well 0.5. The integrated CMOS chip can also include a phase extraction circuit that extracts a phase shift from the received optical signals and delivers the extracted phase shift to the time-to-digital converter. The time-to-digital converter can be configured to provide a localized digital phase output. The time-to-digital converter can include delay cells and an encoder that scans the delay cells to locate the localized digital phase output. The CMOS chips can have a surface area of about 4 mm by 4 mm.

In another aspect, the disclosure features methods for imaging lifetime of fluorescence or luminescence. The methods include receiving optical signals by an imaging region of an integrated complementary metal-oxide semiconductor (CMOS) chip and processing the received optical signals to provide a digital phase output from the integrated CMOS chip. The imaging region can include a photodetector. The received optical signals are processed by converting a time delay to the digital phase output by a time-to-digital converter on the CMOS chip.

The methods for imaging lifetime of fluorescence or luminescence can also include one or more of the following features. The digital phase output can be used for sensing oxygen. The digital phase output can be used for detecting skin cancer. The optical signals can include an excitation signal and a fluorescence or luminescence emission signal, and the received optical signals can be processed by extracting a phase difference between the excitation signal and the emission signal. The received optical signal can be processed by converting the extracted phase difference within a phase domain into a time delay.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

FIG. IC is a block diagram of a system using a chip containing a fluorescence or luminescence lifetime imaging system.

Figure 2A:
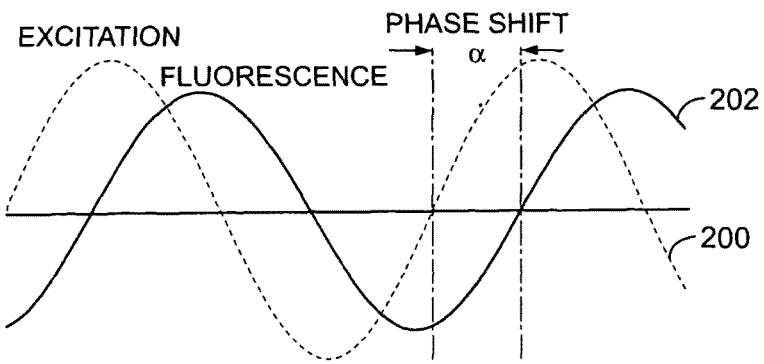

FIG. 2A is a plot of sinusoidal excitation and resultant sinusoidal emission due to fluorescence/luminescence lifetime.

Figure 2B:
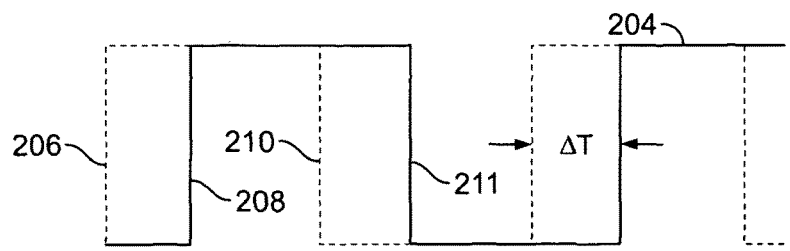

FIG. 2B is a plot of time-domain delay converted from a frequency-domain phase shift.

Figure 3A:
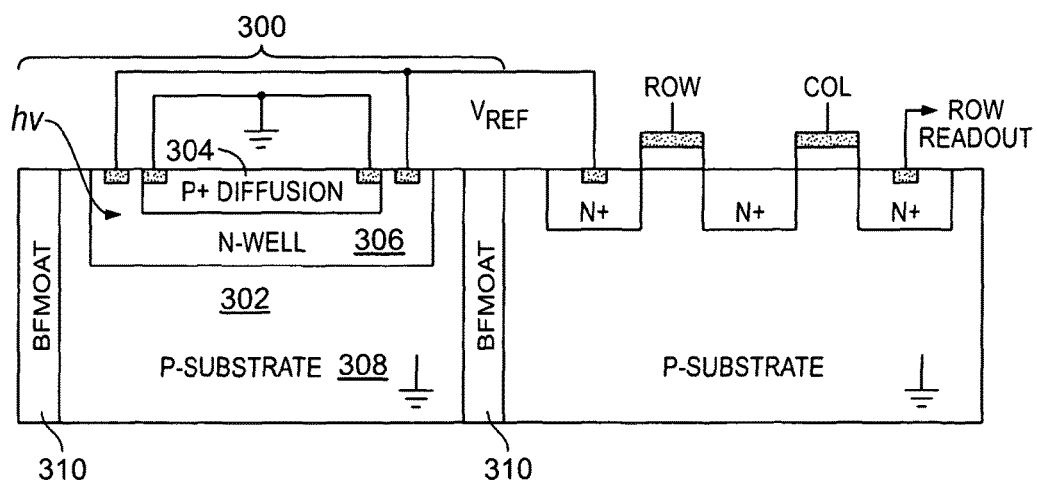

FIG. 3A is a schematic cross-sectional view of a pixel on a chip containing a fluorescence lifetime imaging system.

Figure 3B:
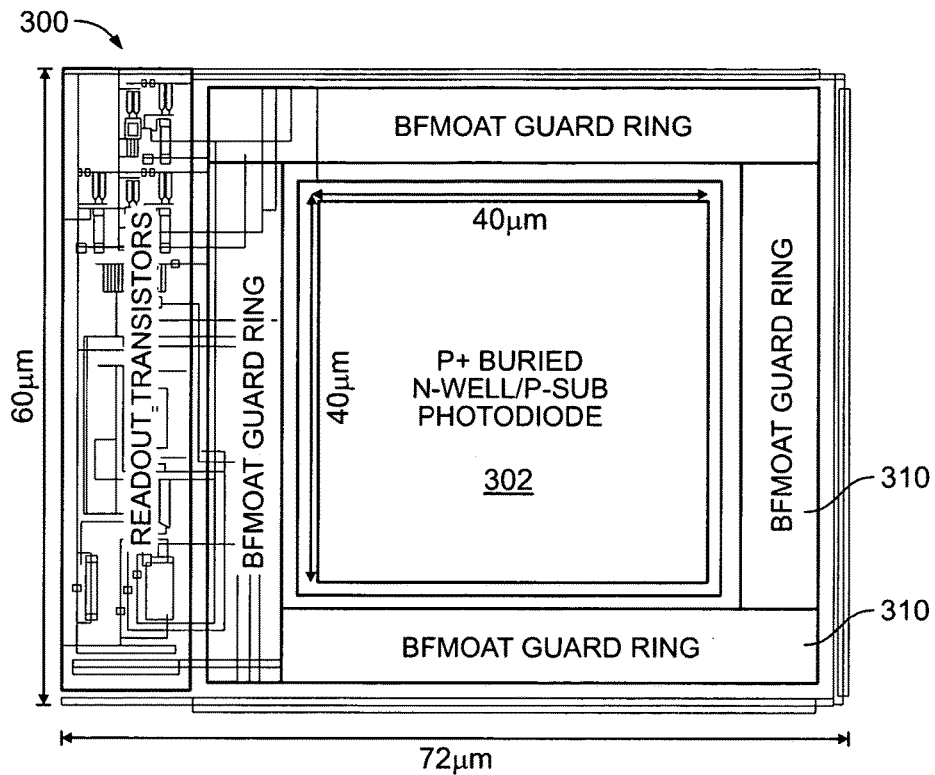

FIG. 3B is a schematic top view of a pixel on a chip containing a fluorescence or luminescence lifetime imaging system.

Figure 4:
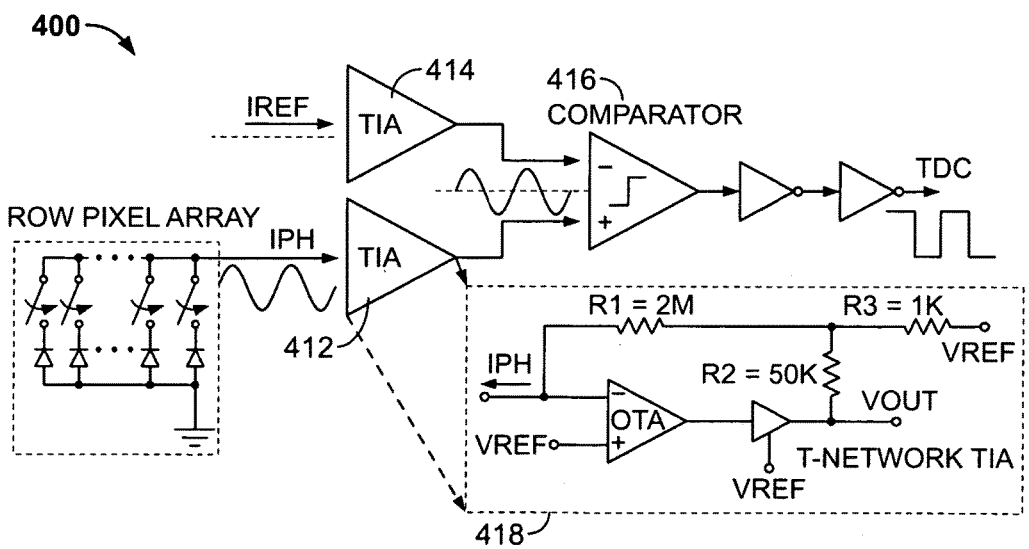

FIG. 4 is a schematic diagram of row-level phase extraction circuit.

Figure 4A:
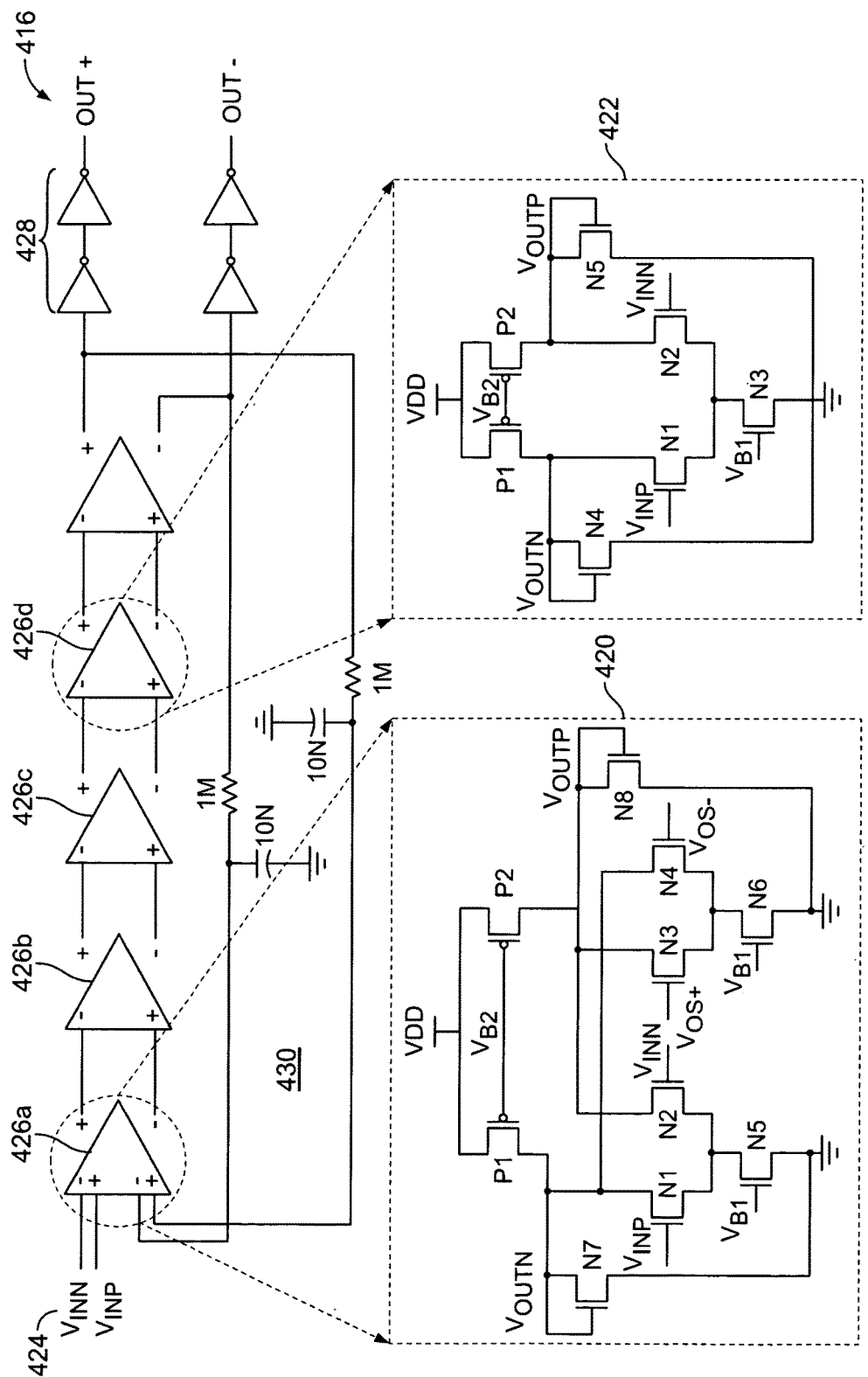

FIG. 4A is a schematic diagram of a comparator circuit.

Figure 5A:
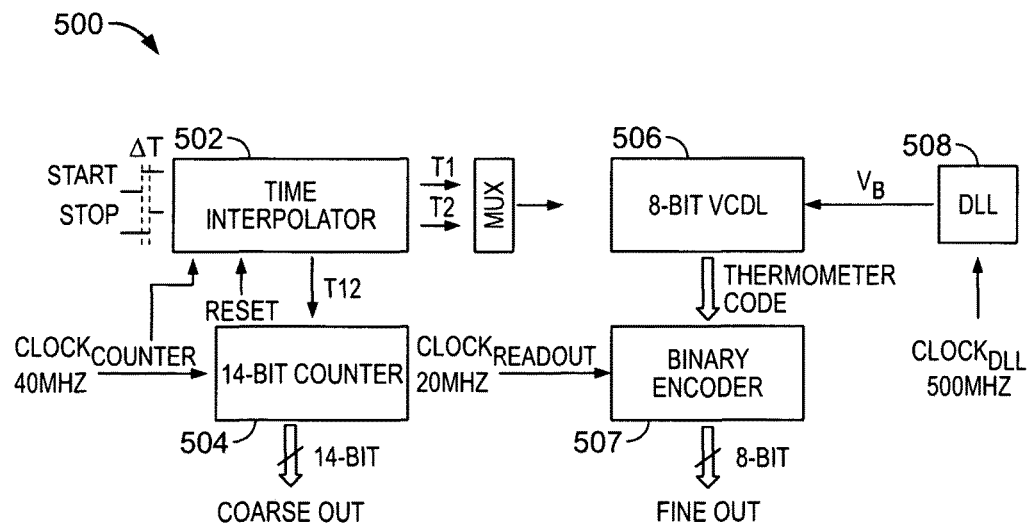

FIG. 5A is a block diagram of a TDC.

Figure 5B:
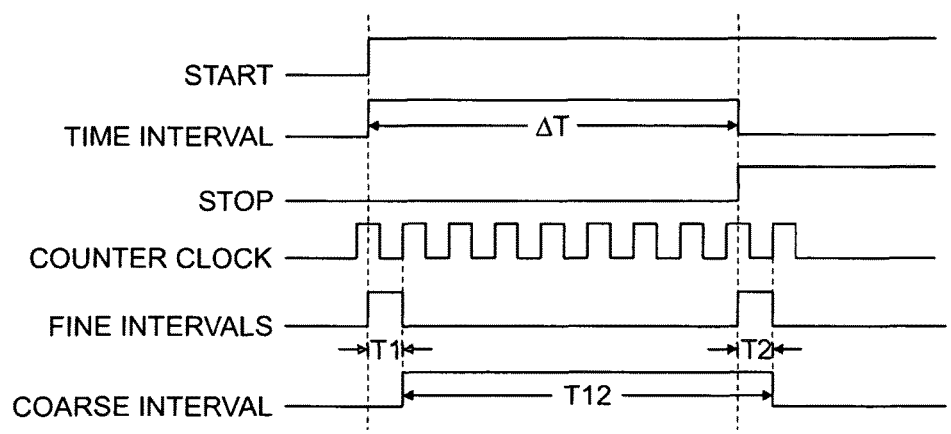

FIG. 5B is a diagram of time interpolation in a TDC.

Figure 5C:
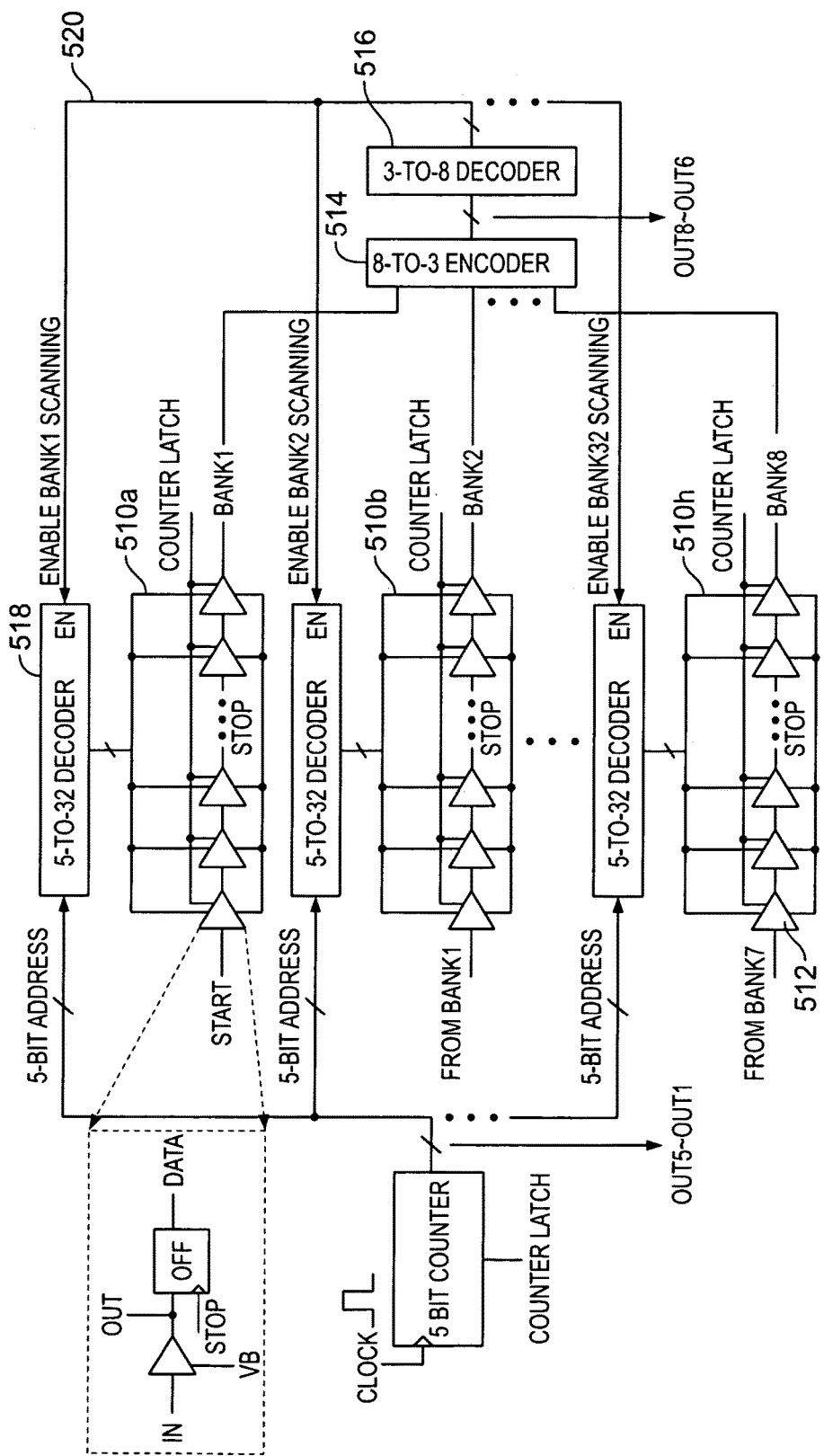

FIG. 5C is a schematic diagram of voltage-controlled delay-line (VCDL)-based fine resolution TDC circuit.

Figure 6:
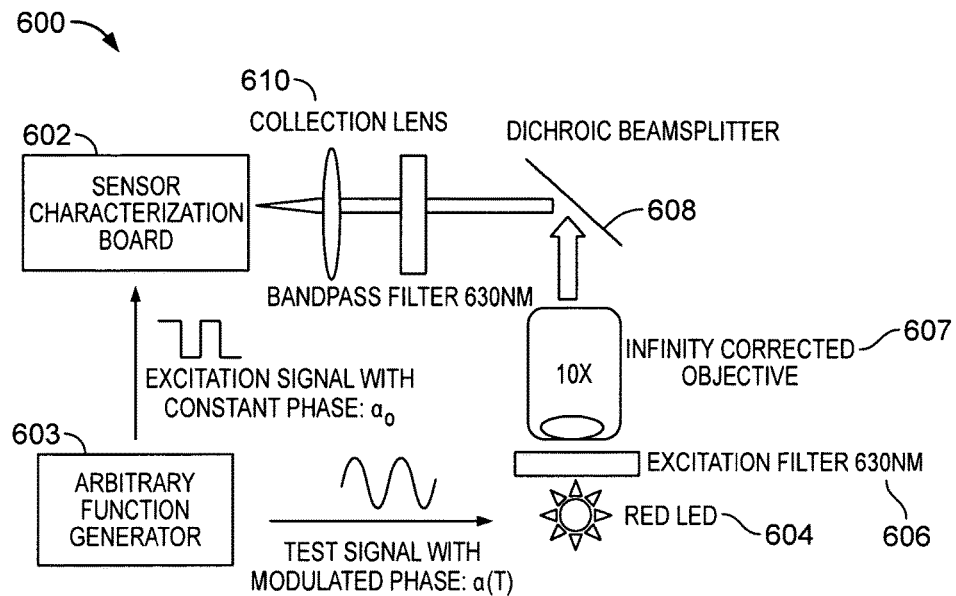

FIG. 6 is a schematic diagram of a system setup for using and/or testing a chip containing a fluorescence lifetime imaging system.

Figure 7A:
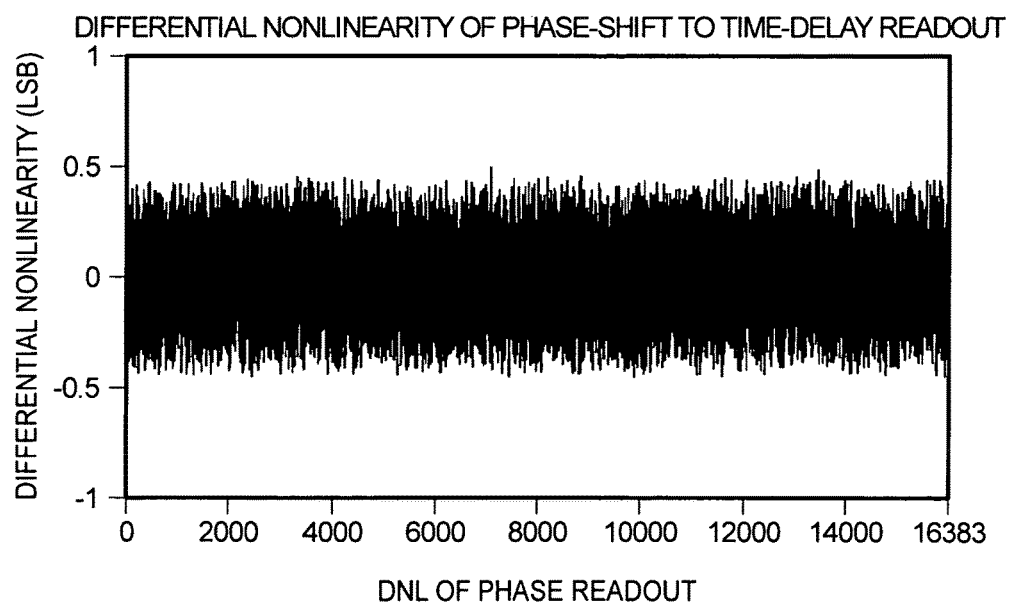
Figure 7B:
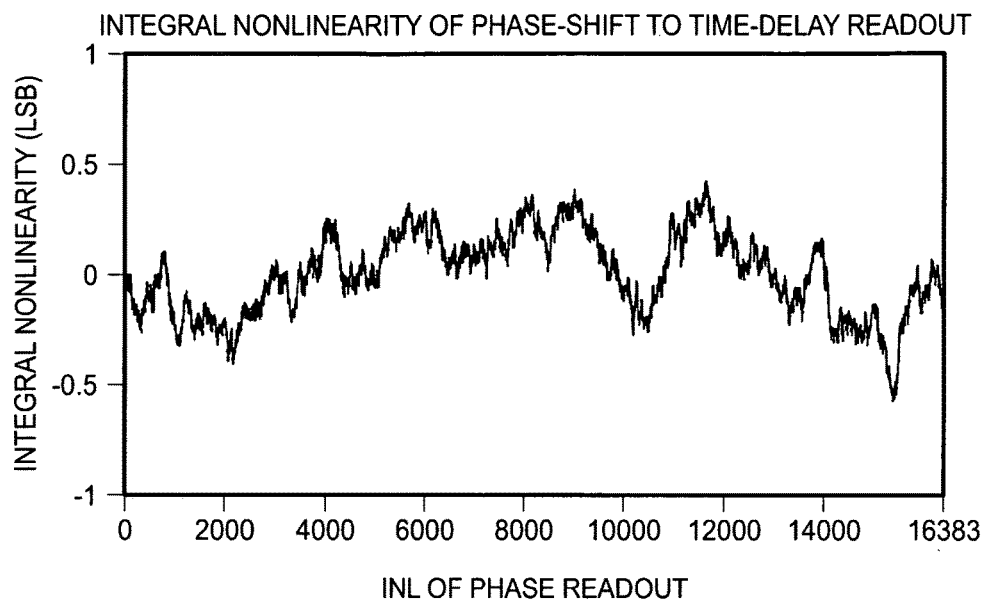

FIGS. 7A and 7B are plots of measured linearity of digital phase readout.

Figure 8A:
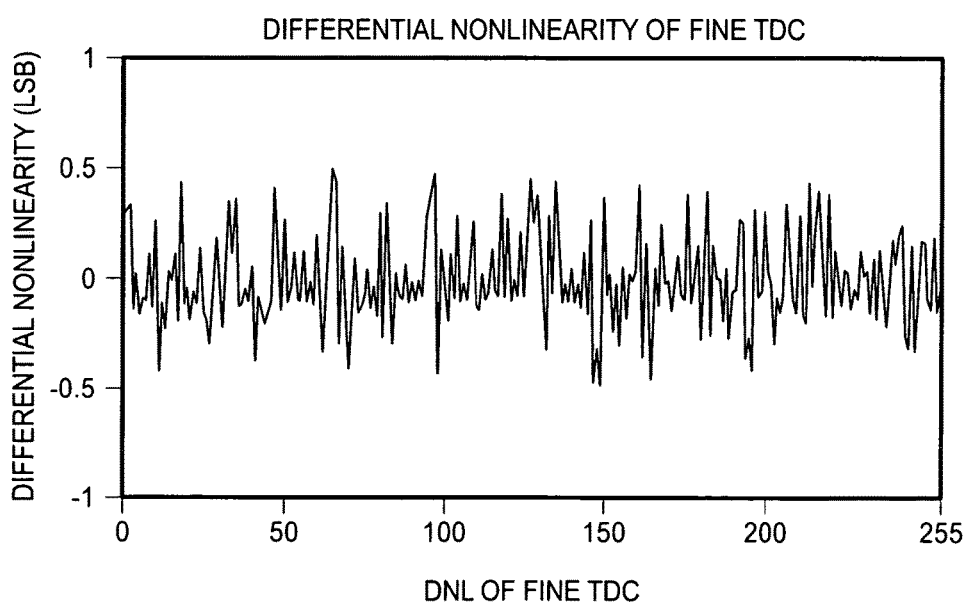
Figure 8B:
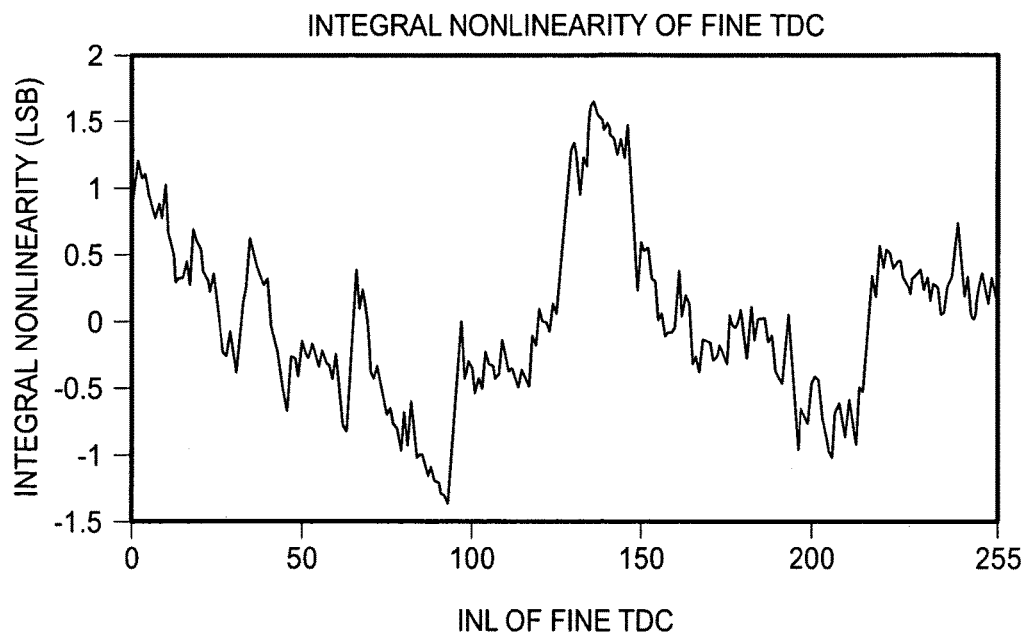

FIGS. 8A and 8B are plots of measured linearity of fine TDC.

FIGS. 9(A)-(D) are phase images.

Figure 10:
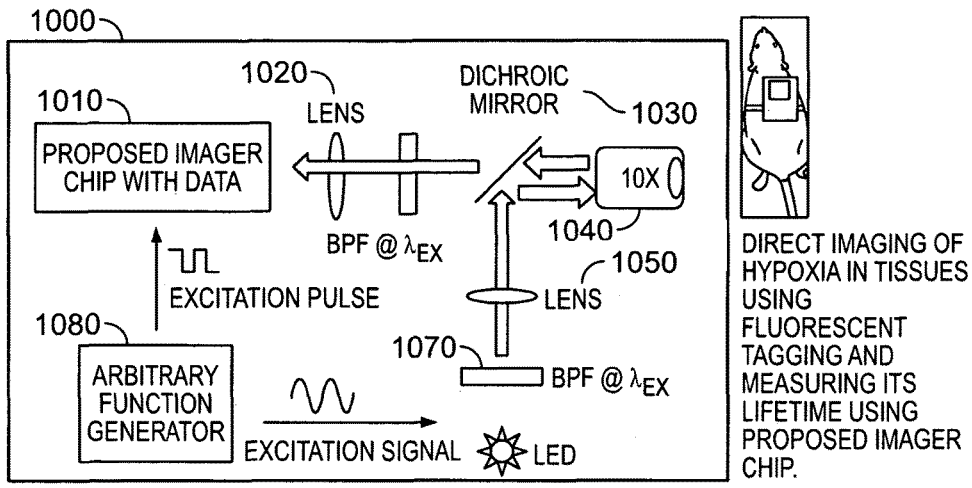
Figure 11:
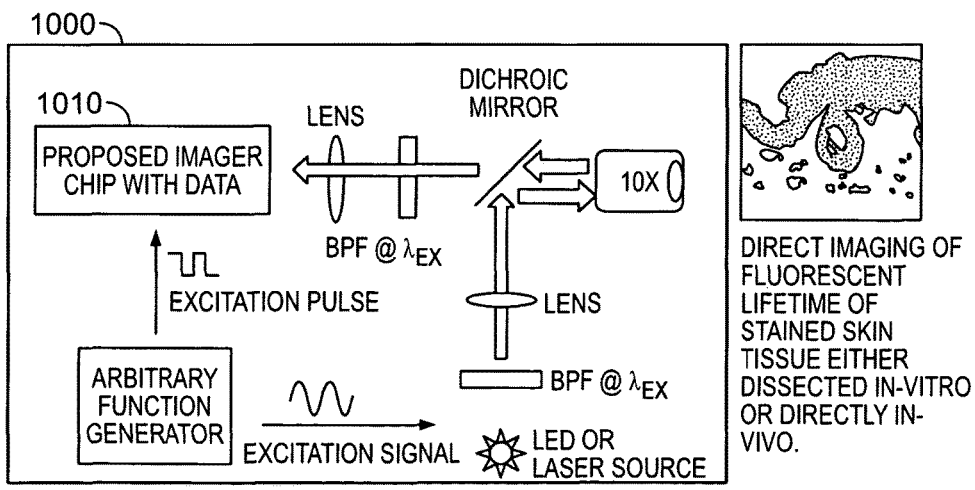

FIGS. 10 and 11 are schematic diagrams of microscopes including a chip containing a fluorescence or luminescence lifetime imaging system for various uses.

Figure 12A:
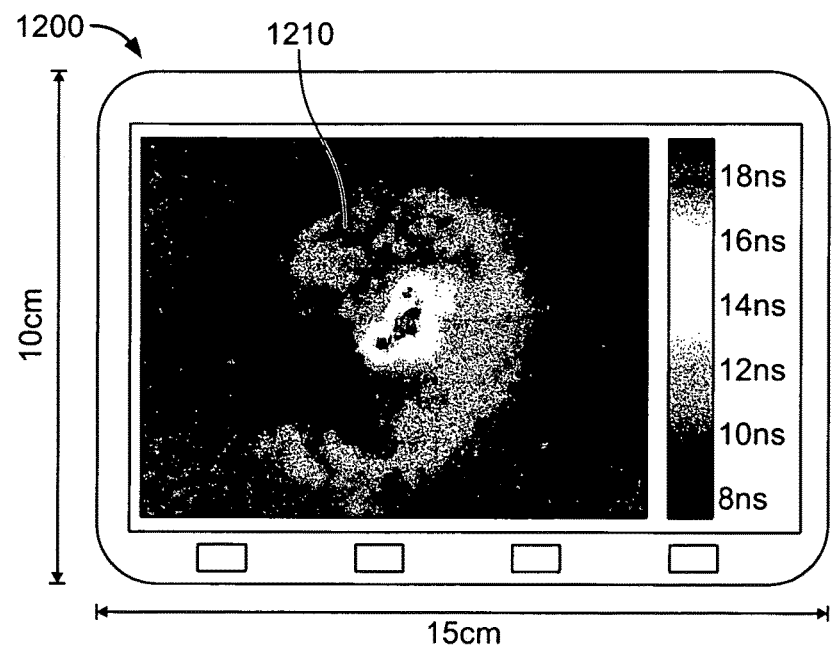

FIG. 12A is a schematic top view of a portable skin cancer scanner including a chip containing a fluorescence lifetime imaging system.

Figure 12B:
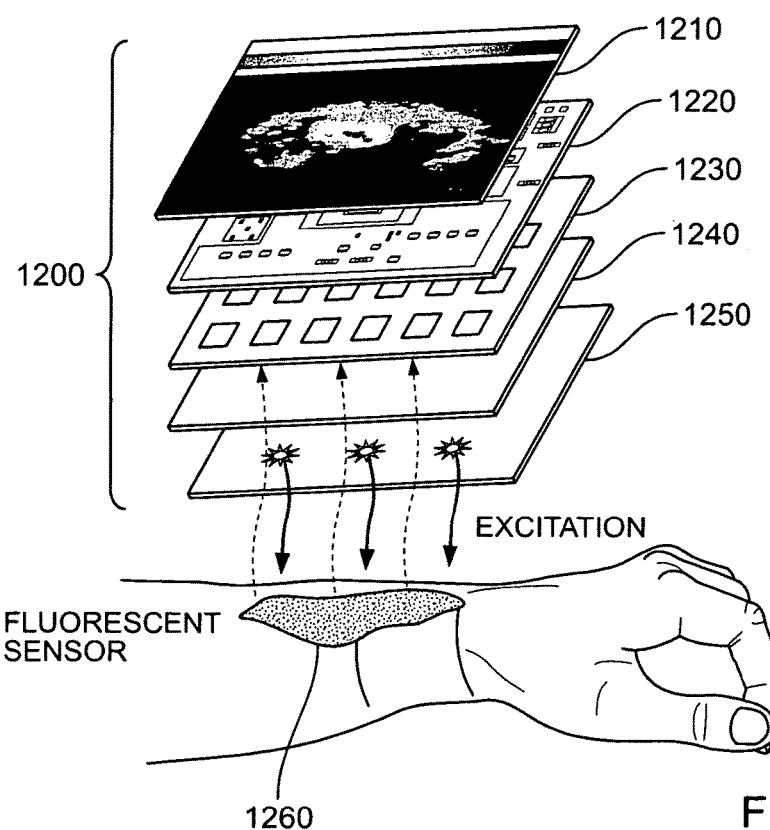

FIG. 12B is a schematic exploded view of a portable skin cancer scanner including a chip containing a fluorescence lifetime imaging system.

DETAILED DESCRIPTION

Fluorescence and/or Luminescence Lifetime Imaging Systems

Figure 1A:
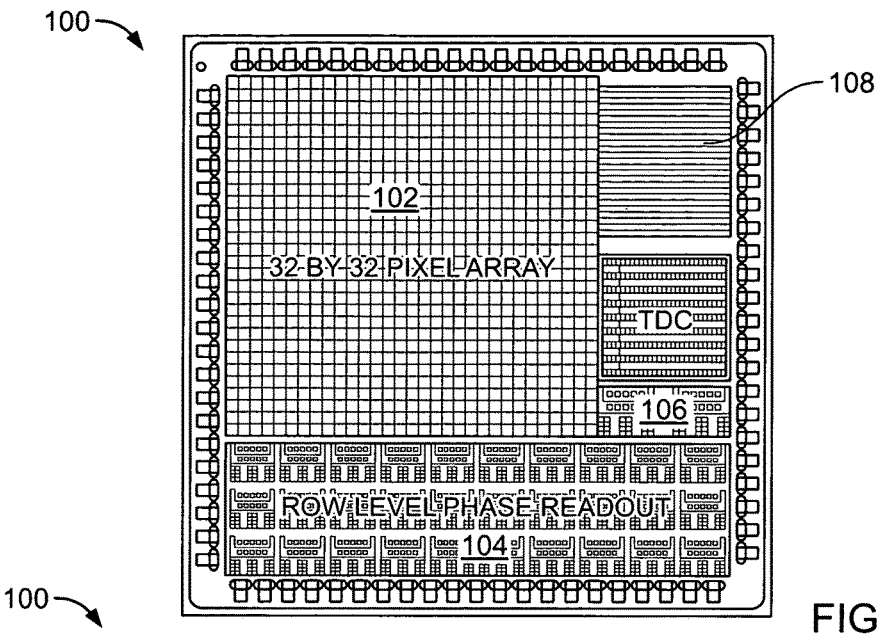
FIG. 1A is a schematic top view of a chip containing a fluorescence or luminescence lifetime imaging system.
Figure 1B:
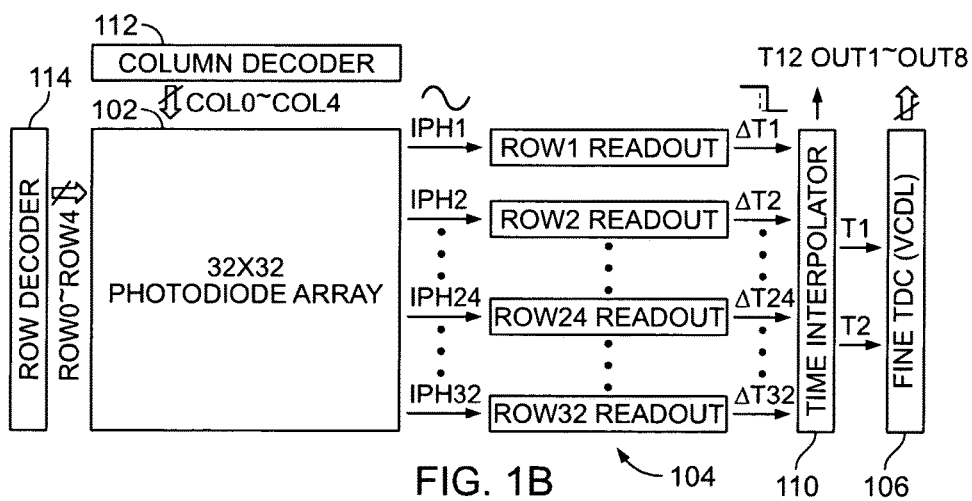
FIG. 1B is a block diagram of a fluorescence or luminescence lifetime imaging system.

Referring to FIGS. 1A and 1B, a fluorescence and/or luminescence lifetime imaging system 100 on a chip 108 includes an imaging region 102 that captures images, e.g., detects photons received from target materials or environments that are marked with fluorescence, and outputs digital phases with a high sensitivity from a TDC 106. The output digital phases contain information regarding the biological or chemical properties of the target materials or environments.

As an example, the use of the chip 108 is shown in FIG. IC. The chip 108 is placed in the vicinity of or in contact with a fluorescently marked target material or one exhibiting autofluorescence in an environment, e.g., a sample or a body part. An off-chip light source 116, e.g., an LED or laser light source, projects light onto the sample 118 and excites fluorescence 120 contained or inherent in the sample 118. Alternatively, an on-chip light source 116' (in dashed lines) can be used for exciting the fluorescence 120. The imaging region 102 of the chip 108 receives measurement signals, e.g., photons, from the excited fluorescence 120 and reference signals, e.g., photons or other signals related to the light source 116 (or source 116'). By processing a phase shift detected for the two different types of signals, e.g., one signal being the excitation signal and the other signal being the emitted fluorescence, the chip 108 outputs phases for the fluorescence lifetime imaging. In some implementations, the chip 108 is incorporated into a device (see, e.g., FIGS. 10, 11, and 12A-12B), e.g., a hand-held device, and the phase is output on a screen of the device.

Referring again to FIGS. 1A and 1B, in some implementations the imaging system 100 implements frequency-domain phase measurements. In particular, the phase shift between the reference signal and the excited fluorescence, luminescence or autofluorescence signal is extracted using a phase extraction circuitry, e.g., row-level phase extraction circuit 104, on the chip 108. The phase shift measured and extracted in frequency-domain is converted into time-domain delay using a high-gain trans-impedance amplifier (TIA) cascaded by a high-speed comparator. The time delay is digitized for phase image reconstruction using the TDC 106. The frequency-domain phase measurements use a low-power light-emitting diode (LED) as an excitation source and are cost-effective and power efficient.

Referring to FIG. 2A, the frequency-domain phase measurement extracts an excitation signal 200 (in dashed lines) and an excited fluorescence signal 202 (in solid lines). The excitation signal 200 has a modulated intensity that can be expressed as:

$$I=I_0 \cdot \{1+k_M \sin(\omega t)\} \quad (1)$$

where I is the optical intensity, $k_M$ is modulation index, and $\omega$ is modulation frequency. The excited fluorescence signal 202 exhibits a phase-shift $\alpha$ from I:

$$F=F_0 \cdot \{1+k_F \sin(\omega t-\alpha)\} \quad (2)$$

where F is the optical intensity, a is a function of fluorescence lifetime $\tau$: $\alpha=\tan^{-1}(\omega\tau)$. When a zero-crossing detection on both the excitation signal 200 and the excited fluorescence signal 202 with respect to their common-mode values $I_0$ and $F_0$, the sine waves are converted to digital square pulses 204 as shown in FIG. 2B. The square pulses 204 have rising edges 206, 208 and falling edges 210, 211 triggered by the zero-crossing points. Based on the square pulses 204, the phase-shift $\alpha$ can be represented in the form of a time-domain delay $\Delta t=\alpha/\omega$, which can be digitally quantized using a TDC, e.g., the TDC 106 on the chip 108 of FIG. 1A. The chip 108 can provide a phase readout with a high sensitivity and a high dynamic range.

The phase-shift between intensity-modulated excitation light and the emitted fluorescence contains fluorescence lifetime information, which can be extracted by analog signal processing, e.g., using lock-in amplifiers. The integration of the frequency-domain phase measurements on the chip 108 provides a low-cost, low-power, and compact platform for fluorescence lifetime imaging, e.g., in field experiments or environment monitoring.

Referring again to FIGS. 1A and 1B, the fluorescence lifetime imaging system 100 is entirely integrated on the monolithic chip 108 having small dimensions. In some implementations, the size can be, e.g., 4 mm by 4 mm. For example, the chip 108 can be a 65 nm CMOS chip having high speed transistors having a high transit frequency $f_T$ property. The components of the COMS chip are integrated at a large scale system level. The direct phase output from the chip 108 has a high sensitivity and the chip 108 operates within a large dynamic range. Other than the imaging region 102, the row-level phase extraction circuit 104 (or "row level phase readout"), and the TDC 106 shown in FIG. 1A, the chip 108 includes other components (discussed below) that enable the chip 108 to provide direct phase readout based on signals received at the imaging region 102. The chip 108 does not require any off-chip signal converters to further process signals to obtain digital phase outputs. Although a circuit design for each component is described below, other circuit designs can be implemented to provide the functions of the chip 108.

In some implementations, the imaging region 102 can include arrays of photodetectors, e.g., photodiodes, phototransistors, or other types of photodetectors, built within the chip 108. Although the figures show a 32×32 photodiode array, other array configurations can be used. Each photodiode is identifiable by an address within the array and expressed as a vector (x, y). Each photodiode is connected to the xth column decoder of column decoders 112 and the yth row decoder of row decoders 114. Detected signals from each photodiode can be independently decoded by the corresponding column decoder and row decoder.

The photon-generated current from each row of photodiodes, $I_{ph1}$~$I_{ph32}$, are processed by the row-level phase extraction circuit 104. The circuit 104 performs a current-to-voltage conversion and uses zero-crossing detection to convert extracted phase shifts into time-domain delays. The time delay for each row of photodiodes, $\Delta t_i$ (i=1~32) is digitally multiplexed into a time interpolator 110 that divides $\Delta t_i$ into fine intervals T1 and T2, and a coarse interval T12. The intervals T1 and T2 are multiplexed into the TDC 106 for fine conversion, and T12 is delivered to an off-chip digital counter (not shown) for coarse conversion. In some implementations, the TDC 106 is a voltage-controlled delay-line (VCDL) based TDC. The digital phase output is obtained by reconstructing combined fine outputs of T1 and T2 and a coarse output of T12. The configurations of the photodiode array, the row-level phase extraction circuit 104, the time interpolator, and the RDC 106 allow the lifetime imaging to be performed within an extended dynamic range while maintaining a high temporal resolution.

Pixels of the Imaging Region

The photodiode array, e.g., a 32 by 32 array, in the imaging region 102 is built by repeating a unit that contains one photodiode and other associated components. We call such a unit a "pixel" of the chip 108. Referring to FIGS. 3A and 3B, a pixel 300 can have a passive pixel architecture for high fill factor, and can include a photodiode 302 that is constructed by a P+ layer buried in an N-well 306 and a P-substrate 308. Such a construction can reduce current leakage. In some implementations, a highly resistive BF-Moat layer 310 can be disposed around the photodiode 302 to isolate noise from the photodiode 302. The BF-Moat layer 302 can also reduce or prevent crosstalk between adjacent pixels (only one pixel shown). In some implementations, the pixel 300 does not include any BF-Moat layers. Other types of pixels, such as those having an active pixel sensor architecture, can be used in the imaging region 102. The photodiode can have other structures, such as P+/N-well, N+/P-SUB, NWELL/PSUB or can be a phototransistor. In one embodiment, the pixel 300 can have a pitch size of about 50 μm. The pixel size should be designed to be relatively large pixel size, e.g., sufficiently large, to provide a high fill factor, e.g., about 37%. The large pixel size also provides a high optical sensitivity for imaging (photon detection). The dimensions shown in FIG. 3B are just examples of one specific embodiment, and can be varied.

Row-Level Phase Extraction Circuits

Referring to FIG. 4, a simplified architecture of one implementation of a row-level phase extraction circuit 400 on the chip 108 is shown. The photon-generated current $I_{ph}$ from each row of photodiodes is amplified and converted to a voltage using a TIA 412. A threshold for zero-crossing detection for compensating background illumination $I_{ref}$ is generated using another TIA 414. A high-speed comparator 416 adjusts the output of TIA 412, a voltage from the photon-generated current $I_{ph}$, based on the output from TIA 414. The phase-shift to be input into the TDC (e.g., the TDC 106 of FIG. 1A) is expressed as time-delay between the excitation signal (e.g., from an external function generator associated with the excitation light) and a row-level zero-crossing output.

The photocurrents $I_{ph}$ and $I_{ref}$ have small magnitudes, e.g., of nA. The TIA 412 includes a T-Network feedback configuration 418 amplify the photocurrent $I_{ph}$. The TIA414 can have a similar configuration. In the T-Network feedback configuration 418 as shown, there are three resistors R1, R2 and R3, where the gain can be set very high with smaller resistors compared to single resistor feedback-based TIA for a similar resistor layout area. In some implementations, a resistive feedback TIA or regulated gate cascade TIA is used instead of the T-network TIA. Other types of TIAs can also be used.

A comparator 416 can include a sequence of cascaded low-gain and high bandwidth pre-amp stages similar to conventional limiting amplifiers to precisely convert the phase shift to a time delay at a high resolution, e.g., a sub-nanosecond resolution. The zero-crossing output has fast rising and falling edges and the comparator 416 introduces a minimum propagation delay to the output. In this implementation, the TIA 412 has a DC gain of 160 dB and 97 pARMS input referred noise integrated over 1 MHz bandwidth. The equivalent gain of the T-Network is expressed in equation (3).

$$V_{OUT}/I_{ph}=R_1+R_2+(R_1 \cdot R_2)/R_3=100\ M\Omega \quad (3)$$

Referring to FIG. 4A, the comparator 416 as shown includes an input-stage 424, four gain-stages 426a-426d, and inverter-based output buffer 428. The gain-stages include sub-circuit blocks 420, 422. An R-C feedback network 430 is implemented to cancel offset and improve stability of the comparator 416. The comparator 416 has a 25 dB gain when the input frequency is about 1 GHz. With an input signal of 100 $mV_{pp}$, the comparator 416 in this implementation has a propagation delay of 1 ns and a rise/fall time of 200 ps. Alternatively, other comparator architectures, such as single stage amplifier or latch based design, can be used.

Time-to-Digital Converter (TDC)

The TDC, e.g., the TDC 106 of FIG. 1A, can be a time interpolated TDC including a VCDL for fine conversion and a digital counter for coarse conversion. Referring to FIGS. 5A and 5B, a TDC 500 includes a time interpolator 502 that takes in Start and Stop signals and divides input time delay Δt from the phase extraction circuit 400 of FIG. 4 into T1, T2, and T12 based on an input clock$_{counter}$ signal. Although the Clock$_{counter}$ signal shown in the figure has a frequency of 40 MHz, the clock$_{counter}$ signal can have other frequencies. The coarse output T12 spans over multiple clock$_{counter}$ cycles and is measured by an off-chip 14-bit digital counter 504. In one implementation, a coarse output having a dynamic range of about 0.4 ms and a temporal resolution of about 25 ns is generated based on the coarse output T12.

A precise measurement of T1 and T2 is carried out using, e.g., an 8-bit VCDL 506 having a sequence of delay cells, e.g., 256 delay cells. Each delay cell is implemented using voltage-controlled delay buffer with digital flip-flop (DFF). An on-chip Delay-Locked-Loop (DLL) 508 regulates a bias voltage $V_b$ of the VCDL 506 to compensate for process variation and performance drift due to temperature and power supply variation. A fine output from the precise measurement of T1 and T2 is produced by a binary encoder 507.

Alternatively, a decoding circuit 520 as shown in FIG. 5C can be used to produce output from the precise measurement of T1 and T2. One particular embodiment is now described. The decoding circuit 520 provides an area-efficient and high-throughput readout of the fine TDC. A delay line in the decoding circuit 520 is grouped into 8 banks 510a-510h, each containing, e.g., 32 delay cells 512. The decoding circuit 520 decodes in a two-step process. First, after a Stop signal latches the location of a Start signal in the delay line, an 8-to-3 encoder 514 outputs three most significant bits OUT8~OUT6 corresponding to one of the 8 banks 510a-510h that holds the Start signal. A 3-to-8 decoder 516 enables a scanning process of the corresponding bank that holds the Start signal to further locate the Start signal within the bank. In particular, a 5-bit counter connected to a 5-to-32 decoder 518 sequentially scans through the delay cells 512 in the bank that holds the Start signal. Then, when the Start signal location is detected, the counter outputs are latched as least significant bits OUT5~OUT1. This localized two-step readout scheme uses at most 32 counter clock cycles for a complete binary encoding of thermometer code generated by the delay line. Thus, the need for complicated routings between individual delay cells 512 in the delay line to a read-only memory (ROM) or counter based decoder circuitry is eliminated. Although 8 banks of 32 delay cells can be used to provide an 8-bit TDC word-length, an arbitrary M-banks of N-delay cells for a word-length of $\log_2(M*N)$ bits, where M and N are integers, can be used.

Examples of System Setup

Figure 1C:
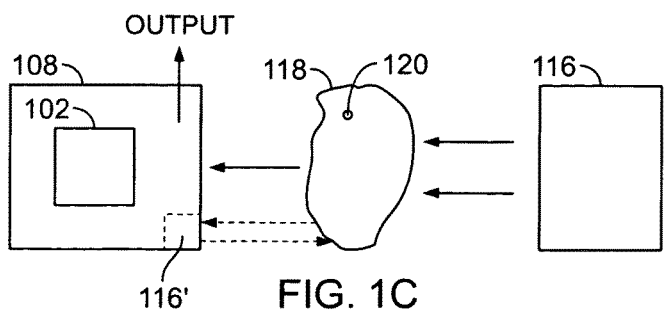

As previously described, the monolithic chip 108 having features described in FIGS. 1A-1B, 2A-3B, 3A-3B, 4, 4A, and 5A-5C can be used in a setup schematically shown in FIG. 1C for fluorescence lifetime imaging. FIG. 6 shows a more detailed device setup 600 for using and/or testing a chip 602 (the same as or similar to the chip 108). The chip 602 images and outputs digital phases based on two input signals, one excitation signal from a two-channel arbitrary function generator 603, and one simulated fluorescence signal from a red LED 604. In addition to generating the excitation signal having a constant phase $\alpha_0$, the function generator also generates a test signal having the same frequency as the excitation signal. The test signal has a modulated phase $\alpha(t)$ and drives a red LED to generate an intensity-modulated optical signal that simulates a fluorescent signal in a sample. In this implementation, the optical signal from the red LED is filtered using 630 nm bandpass filter 606 having a passband of less than 10 nm and is focused using a microscopic objective 607. A dichroic beam splitter 608 guides the focused, filtered light through a correction lens 610 onto the chip 602. The fluorescence lifetime imaging is digitally controlled by a field-programmable gate array (FPGA) such as a Cyclone II FPGA chip (Altera, San Jose, Calif.) and TDC outputs from the chip 602 can be acquired using data acquisition and processing systems, such as LabVIEW (National Instruments, Austin, Tx), for post-signal processing and phase image reconstruction.

In some implementations, the monolithic chip for fluorescence lifetime imaging as described in the previous figures can have the following specification:

| | |
|---|---|
| Basic substrate | 65 nm CMOS |
| Chip surface area | 4 mm × 4 mm |
| Power supply | 1 mA at 1.2 V $V_{DD}$ |
| Photodiode array | 32 × 32 |
| Pixel pitch/fill factor | 50 μm/67% |
| Row phase readout (DNL/INL) | 0.5LSB/0.58LSB, (LSB = 0.01 degrees) |
| Fine TDC (DNL/INL) | 0.49LSB/1.65LSB (LSB = 110 ps) |
| TDC dynamic range | 110 ps~400 μs |

Applications and Uses

The chips for fluorescence and luminescence lifetime imaging have various applications in chemical, biological, and medical fields. Referring to FIG. 10, a chip 1010 can be integrated into an inverted microscope 1000 for use as an oxygen sensing microscope. Such a microscope can be used in in vivo imaging of hypoxia in tissues. In addition to the chip 1010, the microscope 1000 also includes an arbitrary function generator 1080, optics, such as lenses 1020, 1050, mirror 1030, filter 1070, and microscopic object 1040. These components have the same or similar features as those discussed with respect to FIG. 6. Tissues or cells tagged with fluorescent or luminescent markers can be placed within view of the microscope objective 1040. A frequency-modulated LED or laser source is used as an excitation light. The emitted light from fluorescent markers passes through the optics in the microscope and impinges on the chip 1010. The chip images the lifetime of the fluorescent marker and generates an intensity profile. When an oxygen sensing fluorophore, such as ruthenium complex, is used, the imaged fluorescence lifetime provides information on possible oxygenation and hypoxia conditions of the tissues or cells.

Referring to FIG. 11, an inverted microscope 1000 of FIG. 10 can also be used for skin cancer detection, in vitro or in vivo. The target skin tissues and cells are marked with fluorescent markers sensitive to tumor. Changes in fluorescence lifetime caused by the tumor can be imaged by the chip 1010 in the microscope 1000. The phase images may show demarcation of the tissue having the tumor. By comparing the phase images with images of healthy tissues, tumors can be readily detected.

In some implementations, the skin cancer scanner can be a portable device, e.g., a hand-held device. An example of a portable device 1200 is shown in FIG. 12A. The dimensions shown are for one specific example, but can vary. The device 1200 can be in the form of a tablet PC integrated with fluorescence lifetime imaging chip. Referring also to FIG. 12B, the portable device 1200 includes a high resolution liquid crystal display (LCD) 1210 to display the acquired fluorescence lifetime images, a digital signal processor (DSP) board 1220 for pattern recognition and system level control, a digital phase imager 1230, e.g., the chip 108, configured to perform zero-crossing detection algorithm to extract the fluorescence lifetime from biomedical sensors (e.g., fluorescence), an optical filter 1240 to remove the background illumination, and a light emitting diode (LED) array 1250 as an excitation source.

In use, the LED array 1250 excites the fluorescent biomedical sensor that is applied on a target skin area 1260. The emitted fluorescence is filtered and imaged by the digital phase imager 1230. In some implementations, the scanner 1200 has a small size and includes fewer pieces of optics than the microscope 1000 of FIGS. 10 and 11. The scanner 1200 can be placed close to the skin area 1260 to conduct contact imaging without using many pieces of optics in the scanner. Alternatively, a micro-lens at the pixel level can be incorporated into the small scanner 1200. A skin cancer scanner without the present chips for fluorescence and luminescence lifetime imaging is also discussed by R. Cubeddu et al., J. Phys. D: Appl. Phys., vol. 35, pp. R61-R76 (2002), the entire content of which is incorporated herein by reference.

In some implementations, optical signals can be obtained in vivo using, e.g., a camera delivered by a catheter or other devices. The optical signals can be delivered to a chip, e.g., the chip 108 or the chip 1010 through optical fibers. In this implementation, the optics and/or microscope objects of the microscope 1000 may be unnecessary.

EXAMPLES

The following examples are not to be viewed as limiting the inventions, which are described in the claims.

Example 1

Using the setup 600 of FIG. 6, the row-level phase extraction circuit of the imaging system was evaluated via a code density test. To cover the entire temporal dynamic range while maintaining a reasonable phase resolution, the frequency of the excitation signal and the test signal was selected to be 1.2 KHz. A linear phase-shift sweep based on the excitation signal was performed from 0 to 179 degrees at 0.01 degrees per step, producing an equivalent time-domain sweeping range of more than 414 µs with approximately 23 ns per step.

FIGS. 7A and 7B show linearity performance of the photodiode, the TIA, the comparator, and the TDC on the chip. The measured differential nonlinearity (DNL) was 0.5 LSB and the measured integral nonlinearity (INL) was 0.58 LSB. The TDC was characterized using off-chip programmable delay line with dynamic range from 10 ps to 50 ns. Results of the code density test were plotted in FIGS. 8A and 8B, showing a DNL of 0.49 LSB and an INL of 1.65 LSB.

Example 2

Figure 9:
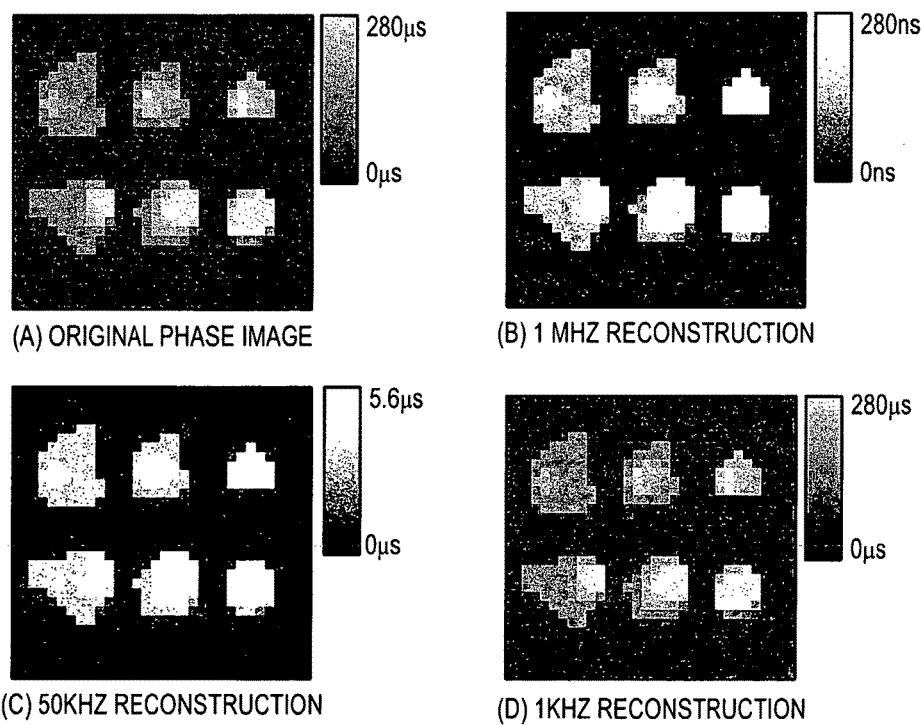

A phase image was reconstructed to demonstrate the phase readout scheme of a chip containing a fluorescence imaging system. A time-resolved fluorescence lifetime image from an oxygen sensor was used as an example phase image (FIG. 9(A)) and was used for generating a 32×32 array of 8-bit phase shift (0 to 100 degrees) pattern according to the image intensity. A one-to-one mapping between the phase shift pattern generated from the example phase image and output phase from the setup 600 of FIG. 6 was performed. Using the setup 600, phase-shift outputs were obtained by scanning the entire 32×32 pixel array. 8-bit gray-scale phase images were reconstructed based on the phase-shift outputs. FIG. 9(A) shows the original example phase image representing fluorescence lifetime from 0 to 280 µs. FIGS. 9(B)-(D) show reconstructed phase images by modulating both the excitation signal and the test signal at frequencies of 1 KHz, 50 KHz, and 1 MHz, respectively. The measurable lifetime covered a wide temporal range, e.g., 0-280 ns in FIG. 9(B) and 0-280 µs in FIG. 9(D).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for use in fluorescence or luminescence lifetime imaging, the device comprising:
   a chip comprising:
   an imaging region comprising a photodetector for receiving a first optical signal corresponding to excitation light from a light source, and a second optical signal corresponding to emitted fluorescence or luminescence from a sample; and
   a time-to-digital converter for providing digital phase output based on the first and second optical signals, wherein the digital phase output corresponds to a temporal offset between waveforms corresponding to the excitation light and the emitted fluorescence or luminescence from the sample.

2. The device of claim 1, wherein the imaging region comprises an array of photodetectors.

3. The device of claim 1, wherein the chip comprises an integrated complementary metal-oxide semiconductor (CMOS) chip, and wherein the CMOS chip further comprises a phase extraction circuit that extracts a phase shift from the first and second optical signals and delivers the extracted phase shift to the time-to-digital converter.

4. The device of claim 1, wherein the time-to-digital converter is configured to provide a localized digital phase output.

5. The device of claim 4, wherein the time-to-digital converter comprises one or more delay cells and an encoder that scans the delay cells to locate the localized digital phase output.

6. The device of claim 1, wherein the chip has a surface area of about 4 mm by 4 mm.

7. A microscope comprising:
   a lens; and
   an integrated complementary metal-oxide semiconductor (CMOS) chip comprising:
   an imaging region comprising a photodetector for receiving a first optical signal corresponding to excitation light from a light source, and a second optical signal corresponding to emitted fluorescence or luminescence from a sample that passes through the lens; and
   a time-to-digital converter for providing digital phase output based on the first and second optical signals, wherein the digital phase output corresponds to a temporal offset between waveforms corresponding to the excitation light and the emitted fluorescence or luminescence from the sample.

8. The microscope of claim 7, wherein the microscope is an oxygen sensing microscope that further comprises an arbitrary function generator.

9. The microscope of claim 7, wherein the imaging region comprises an array of photodetectors.

10. The microscope of claim 7, wherein the integrated CMOS chip further comprises a phase extraction circuit that extracts a phase shift from the first and second optical signals and delivers the extracted phase shift to the time-to-digital converter.

11. The microscope of claim 7, wherein the time-to-digital converter is configured to provide a localized digital phase output.

12. The microscope of claim 11, wherein the time-to-digital converter comprises delay cells and an encoder that scans the delay cells to locate the localized digital phase output.

13. The microscope of claim 7, wherein the CMOS chip has a surface area of about 4 mm by 4 mm.

14. A scanner for use in detecting skin cancer, the scanner comprising:
an integrated complementary metal-oxide semiconductor (CMOS) chip comprising:
an imaging region comprising a photodetector for receiving a first optical signal corresponding to excitation light from a light source, and a second optical signal corresponding to emitted fluorescence or luminescence from a sample; and
a time-to-digital converter for providing digital phase output based on the first and second optical signals, wherein the digital phase output corresponds to a temporal offset between waveforms corresponding to the excitation light and the emitted fluorescence or luminescence from the sample; and
a display for displaying the digital phase output from the integrated CMOS chip.

15. The scanner of claim 14, wherein the scanner is portable.

16. The scanner of claim 15, wherein the scanner is sized and configured to be hand-held.

17. The scanner of claim 14, wherein the imaging region comprises an array of photodetectors.

18. The scanner of claim 14, wherein the integrated CMOS chip further comprises a phase extraction circuit that extracts a phase shift from the first and second optical signals and delivers the extracted phase shift to the time-to-digital converter.

19. The scanner of claim 14, wherein the time-to-digital converter is configured to provide a localized digital phase output.

20. The scanner of claim 19, wherein the time-to-digital converter comprises delay cells and an encoder that scans the delay cells to locate the localized digital phase output.

21. The scanner of claim 14, wherein the CMOS chip has a surface area of about 4 mm by 4 mm.

* * * * *